United States Patent [19]
Frankel et al.

[11] Patent Number: 4,499,723
[45] Date of Patent: Feb. 19, 1985

[54] TRIS(2-AZIDOETHYL)AMINE AND METHOD OF PREPARATION THEREOF

[75] Inventors: Milton B. Frankel, Tarzana; Edgar R. Wilson, Simi Valley, both of Calif.

[73] Assignee: Rockwell International Corporation, El Segundo, Calif.

[21] Appl. No.: 401,476

[22] Filed: Jul. 26, 1982

[51] Int. Cl.³ .................. C06D 5/08; C07C 117/00
[52] U.S. Cl. ................................ 60/211; 260/349
[58] Field of Search .................... 260/349; 60/211

[56] References Cited

U.S. PATENT DOCUMENTS

| | | | |
|---|---|---|---|
| 2,254,940 | 9/1941 | Endres | 260/349 |
| 2,769,819 | 11/1956 | Sommers et al. | 260/349 |
| 2,853,486 | 9/1958 | Sarett et al. | 260/349 |
| 3,082,598 | 3/1963 | Mahan | 60/35.4 |
| 3,122,570 | 2/1964 | Stansbury et al. | 260/349 |
| 3,636,062 | 1/1972 | Singer | 260/349 |
| 3,700,393 | 10/1972 | Mueller | 60/214 |
| 4,141,910 | 2/1979 | Flanagan et al. | 260/349 |

OTHER PUBLICATIONS

Degering, "An Outline of Organic Nitrogen Compounds", (1945), p. 286, Univ. Lithoprinters, Ypsilanti, Mich.

*Primary Examiner*—Joseph Paul Brust
*Attorney, Agent, or Firm*—H. Fredrick Hamann; Harry B. Field

[57] ABSTRACT

A new compound tris(2-azidoethyl)amine, N-$(CH_2CH_2N_3)_3$, and its method of preparation is disclosed. The subject azido derivative of a tertiary amine has the empirical formula $C_6H_{12}N_{10}$.

3 Claims, No Drawings

4,499,723

TRIS(2-AZIDOETHYL)AMINE AND METHOD OF PREPARATION THEREOF

BACKGROUND OF THE INVENTION

1. Field of the Invention

This invention pertains to a new tertiary amine compound and its method of preparation. More specifically, energetic liquid fuels have been invented for liquid bipropellant systems wherein the fuels are azido derivatives of tertiary amines.

2. Description of the Prior Art

Current storable liquid bipropellant systems are based on using storable liquid oxidizers such as nitrogen tetroxide (NTO), 75NTO/25NO(MON) (75% nitrogen tetroxide/25% nitric oxide), and inhibited red fuming nitric acid (IRFNA) and storable liquid fuels such as hydrazine derivatives and hydrocarbons. The liquid rocket fuels should have the following desired properties: (1) high energy and density, (2) wide liquid range, (3) minimum hydrogen content, and (4) hypergolic with NTO, MON, or IRFNA. Hydrazine derivatives have higher energy than hydrocarbons and are the preferred liquid rocket fuels. In particular, monomethylhydrazine (MMH) is the current fuel of choice because of its low freezing point. However, higher energy fuels are required.

Besides the requirement for higher energy, increasing importance is being placed on the development of minimum smoke liquid bipropellants. Minimum smoke propellants produce virtually no primary smoke and little or no strong nucleation for secondary smoke, but continue to produce water vapor as a combustion product. Hydrogen containing oxidizers and fuels produce water vapor in the exhaust plume, directly and by secondary combustion with atmospheric oxygen. Under some "con-trail" conditions, this water vapor will condense and produce a fog even in the absence of a potent nucleator-like hydrogen chloride. A much wider range of "smoke-free" conditions and a slower formation of this secondary smoke/fog are typical, however, as compared to the behavior of plumes containing large quantities of hydrogen chloride or other strong nucleators. The following criteria can be established for defining the types of oxidizers and fuels that would be most desirable for achieving a minimum smoke liquid bipropellant system:

1. Use no metal ingredients—the major contributors to primary smoke.
2. Eliminate halogen containing incredients so that no HCl or HF would be formed as combustion products.
3. Reduce hydrogen content—to minimize formation of water.
4. Maximize formation of CO, $CO_2$, and $N_2$ as the major combustion products.

In evaluating candidate liquid bipropellant systems that would have minimum smoke, two critical parameters were selected as the criteria. One was the specific impulse density ($I_d$), and the other was the formation of secondary smoke caused by the condensation of water vapor. Both the mole percent of $H_2$ and $H_2O$ in the combustion products is important since hydrogen will react with ambient oxygen to form water.

SUMMARY OF THE INVENTION

Accordingly, there is provided by the present invention a new minimum smoke energetic liquid fuel for use in a bipropellant system. The new compound, tris(2-azidoethyl)amine, is an azido derivative of a tertiary amine and has the structural formula $N-(CH_2CH_2N_3)_3$. The method for producing the new fuel is also disclosed.

OBJECTS OF THE PRESENT INVENTION

Therefore, it is an object of the present invention to provide a new tertiary amine.

A further object of the present invention is to provide a method of making the tertiary amine.

Still a further object of the present invention is to provide a minimum smoke energetic liquid fuel.

Yet a further object is to provide a liquid fuel capable of replacing monomethyl hydrazine.

Another object of the present invention is to provide an energetic fuel for use in a liquid bipropellant system.

Yet another object of the present invention is to provide a new liquid rocket fuel.

Still another object of the present invention is to provide a new liquid gun propellant.

A further object of the present invention is to effect an increase in density impulse of liquid bipropellant systems.

Another object of the present invention is to provide a fuel that will provide a significant improvement in the plume signature of liquid bipropellant systems.

Other objects, advantages and novel features of the present invention will become apparent from the following detailed description of the invention.

DESCRIPTION OF THE PREFERRED EMBODIMENTS

In accordance with the present invention, there is provided a new azido derivative of a tertiary amine. The new compound is tris(2-azidoethyl)amine (TAEA) and has the following structural formula:

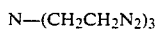
$$N-(CH_2CH_2N_2)_3$$

Tris(2-azidoethyl)amine is a minimum smoke energetic fuel for use in liquid bipropellant systems such as rocket propulsion system and gun propulsion systems. Table I shows that the TAEA is a relatively insensitive, high energy, high density liquid fuel which is hypergolic with liquid oxidizers such as NTO, MON, and IRFNA.

Comparative theoretical performance calculations were carried out on the current $N_2O_4$/MMH bipropellant system with the $N_2O_4$/TAEA system. The data, as summarized in Table II, show that a gain of about 7.39% in density impulse can be achieved by the replacement of MMH with TAEA.

TABLE I

| DATA SHEET ON TAEA | |
|---|---|
| Name: | tris(2-azidoethyl) amine |
| Code: | TAEA |
| Structure: | $N-(CH_2CH_2N_3)_3$ |
| Formula: | $C_6H_{12}N_{10}$ |
| Molecular Weight: | 224 |
| Refractive Index (25C) | 1.5090 |
| Impact Sensitivity (in-lb): | 60–65 (TMETN = 25–30) |
| Density: | 1.162 |
| Freezing Point (C.): | −19 |
| $\Delta H_f$(Kcal/mole): | +212 |
| Hypergolic with | Positive |

TABLE I-continued

DATA SHEET ON TAEA $N_2O_4$:

TABLE II

THEORETICAL PERFORMANCE CALCULATIONS ON
$N_2O_4$/MMH AND $N_2O_4$/TAEA BIPROPELLANT SYSTEMS

| Fuel | M/R | ISP | IspD | % Gain |
|------|-----|-----|------|--------|
| MMN  | 2.15 | 288.7 | 346.4 | |
| TAEA | 1.6  | 282.7 | 371.8 | 7.39 |

Comparative theoretical performance calculations were carried out on liquid bipropellant systems using 75NTO/25NO(MON) as the oxidizer and MMH and TAEA as the fuels. The data, as summarized in Table III, show that the replacement of MMH with TAEA can provide not only a gain of 8.1% in density impulse but also a 44.2% reduction in $H_2$ and $H_2O$ as combustion products.

TABLE III

THEORETICAL PERFORMANCE CALCULATIONS
ON CANDIDATE LIQUID BIPROPELLANT SYSTEMS

| Candidate | MR | $I_{opt}$ $I_{opt}$ 1000 + 14.7 | $I_d$ | % Increase In $I_d$ | CO | $CO_2$ | $N_2$ | $H_2$ | $H_2O$ | $H_2 + H_2O$ | % Reduction in $H_2 + H_2O$ |
|-----------|-----|--------|-------|-------|-----|--------|-------|-------|--------|--------------|------------------------------|
| MON/MMH   | 2.3 | 289.7  | 338.7 | 0     | 5.5 | 10.4   | 36.5  | 5.0   | 42.5   | 47.5         | 0                            |
| MON/TAEA  | 1.8 | 284.4  | 366.1 | 8.1   | 13.1 | 18.1  | 41.9  | 3.1   | 23.4   | 26.5         | 44.2                         |

Thus, as previously noted, the performance and plume signature of the state-of-the-art liquid bipropellant rocket systems can be significantly improved by replacing MMH or other hydrazine derivatives with the compound of this invention.

The tris(2-azidoethyl)amine of this invention is readily prepared in a simple process from the commercially available, low-cost triethanolamine, according to the following equations:

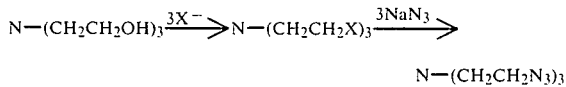

$$N-(CH_2CH_2N_3)_3$$

wherein X=halide, nitrate, or tosylate

In the first step, triethanolamine is converted to the trinitrate, trihalide, or tritosylate, reacting it with the appropriate anion by well-established procedures. In the newly invented reaction step, the tris(2-haloethyl)amine, tris(2-nitratoethyl)amine, or tris(2-tosylethyl)amine is reacted with an ionic azide such as the preferred sodium azide, or lithium azide or the like. The reaction can most expeditiously be carried out in dipolar aprotic solvents. Such as dimethylformamide or dimethylsulfoxide, which are used routinely as a media for azide ion substitution reactions. The reaction temperature can range from 25° to 95° C. The preferred range is 50°–95° C. The reaction can also be carried out in aqueous medium using a phase transfer catalyst.

By way of illustration and not limitation, the following example is given:

EXAMPLE

Preparation of Tris(2-azidoethyl)amine 35.2 g (0.17 mole) 2,2',2" trichloroethylamine (dist b.p. 77° C., 0.07 mm, $N_{25}^D$1.4239) was combined with 37.0 g (0.57 moles) sodium azide in 100 ml dry dimethylformamide in a 250 ml, single-necked round-bottom flask which was equipped with a mechanical stirrer, sidearm adapter, reflux condenser, and oil heating bath. The reaction mixture was heated to 95° C. and stirred for two hours. At the end of this time, a gas chromatographic analysis indicated the reaction to be complete. The reaction mixture was allowed to cool to room temperature and then was dumped into one liter of water with vigorous stirring and 100 ml of chloroform was added. The organic solution was separated and washed six times with water to remove dimethyl formamide. The chloroform solution was dried over anhydrous sodium sulphate, then passed through a neutral alumina column to yield a colorless solution. This was stripped of solvent to yield 31.8 g (83%) of pale yellow oil $N_{25}^D$1.5090. Gas chromatographic analysis of this material shows it to be more than 99% pure. An infrared spectrogram was consistent with the expected structure.

A sample was submitted for elemental analysis. Calculated for $C_6H_{12}N_{10}$ C=32.14, H=5.39%, N-62.47%, found C=32.28%, H=5.37%, N=62.56%. The freezing point of this material was found to be −19° C. and its density 1.16 g/cc. This material is hypergolic with nitrogen tetroxide and has an impact sensitivty of 63 in-lb.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A compound of the formula $N-(CH_2CH_2N_3)_3$.
2. A method of propulsion comprising reacting a tris(2-azidoethyl) amine fuel with a liquid oxidizer.
3. The method of claim 2 wherein said liquid oxidizer is selected from the group consisting of nitrogen tetroxide, inhibited red fuming nitric acid and 75% nitrogen tetroxide/25% nitric oxide.

* * * * *